United States Patent
Rahman et al.

[11] Patent Number: 5,560,923
[45] Date of Patent: Oct. 1, 1996

[54] METHOD OF ENCAPSULATING ANTHRACYCLINE IN LIPOSOMES

[75] Inventors: Aquilur Rahman, Gaithersburg, Md.; Alain Thierry, Washington, D.C.; Anatoly Dritschilo, Bethesda, Md.

[73] Assignee: Georgetown University, Washington, D.C.

[21] Appl. No.: 314,543

[22] Filed: Sep. 28, 1994

Related U.S. Application Data

[63] Continuation of Ser. No. 939,609, Sep. 2, 1992, abandoned.
[51] Int. Cl.$^6$ ................................................. A61K 9/127
[52] U.S. Cl. ........................... 424/450; 264/4.1; 264/4.6
[58] Field of Search ............................... 424/450; 264/4.1, 264/4.6

[56] References Cited

U.S. PATENT DOCUMENTS

| | | | |
|---|---|---|---|
| 4,419,348 | 12/1983 | Rahman et al. | 424/180 |
| 4,898,735 | 2/1990 | Barenholz et al. | 424/450 |
| 4,906,477 | 3/1990 | Kurono et al. | 424/450 |

*Primary Examiner*—Jyothsna Venkat
*Attorney, Agent, or Firm*—Foley & Lardner

[57] ABSTRACT

A method of preparing a liposomal anthracycline glycoside composition, which entails forming cardiolipin-containing liposomes by drying a lipid mixture containing cardiolipin, and then introducing an aqueous solution, and mixing the cardiolipin-containing liposomes with a solution of anthracycline glycoside.

27 Claims, 4 Drawing Sheets

METHOD OF ENCAPSULATING ANTHRACYCLINE IN LIPOSOMES

This application is a continuation of application Ser. No. 07/939,609, filed Sep. 2, 1992, now abandoned

BACKGROUND OF THE INVENTION

1. Field of the Use

The present invention relates to a method of encapsulating anthracycline glycosides in liposomes and liposomal compositions obtainable thereby.

2. Description of the Background

Anthracycline glycosides are compounds which are known to exhibit both antibiotic and anticancer activity. Generally, anthracycline glycosides contain an amino-sugar linked to a tetrahydronaphthacene chromophore by a glycoside bond. Among this group of compounds are doxorubicin (adriamycin, a product of U.S. Pat. No. 3,590,028) and daunorubicin (U.S. Pat. No. 4,012,284) as well as analogs described in U.S. Pat. No. 3,686,136 and Yamamoto, K. et al., *J. Med. Chem.* 15, 872 (1973); German patent nos. 2,327,211; 2,557,537; and 1,920,198; Bachman, E. et al., *Agents and Actions*, 5/4, 383, 1975); Chandra, P., *Cancer Chemotherapy*, Rep. 6,115 (1975); Arcamone, F. et al., id. at 123; and Zbinden, G. et al., *Cancer Chemotherapy*, Rep. 4, 707 (1975).

Doxorubicin is one of the most commonly used antineoplastic agents and has demonstrated activity for a wide range of human cancers such as leukemia, lymphoma and solid tumors. The mechanisms of action of anthracycline glycosides are considered to involve the blocking of the functions of deoxyribonucleic acid (DNA) by intercalation in the DNA structure. Unfortunately, clinical use of these compounds is severely hampered by dose-limiting cardiotoxic effects. The cardiotoxicity of both doxorubicin and daunorubicin has been well documented. Further, the cardiotoxic effect has been shown to be cumulative and may lead to congestive heart failure. This cardiotoxicity is quite specific and pharmacologic distribution studies have shown a selective tropism to the heart muscle.

Attempts to prevent anthracycline glycoside cardiotoxicity have included reliance on combination chemotherapy to produce additive or synergistic effects so that the cumulative dosage of the anthracycline glycosides can be reduced, and concomitant administration of antioxidants to protect against cardiotoxic effects.

More recently, liposome delivery systems have been used to reduce anthracycline uptake in cardiac tissue, while preserving drug activity. See for example, U.S. Pat. No. 4,419,348. In using this methodology, it is found that doxorubicin in cardiolipin containing liposome exerts antitumor activity at doses that cause fewer myocardial alterations than the same dose of free doxorubicin. For example, prevention of doxorubicin cardiotoxicity in beagles by liposomal encapsulation has also been shown. Generally, the preparation of this form of doxorubicin involves a two-step preparation process, which entails complexing of the drug with cardiolipin and subsequently encapsulating the complex in liposomes. However, this preparation is very difficult to manage at an industrial level, particularly in conserving good encapsulation efficiency and preserving anthracycline glycoside stability.

Hence, a need exists for a method of preparing liposomal doxorubicin compositions which conserves good encapsulation efficiency while preserving anthracycline glycoside stability.

SUMMARY OF THE INVENTION

Accordingly, it is an object of the present invention to provide a method for producing a anthracycline glycoside composition which affords good encapsulation efficiency.

It is also an object of the present invention to provide a method for producing a anthracycline glycoside composition which preserves anthracycline glycoside stability.

It is also an object of the present invention to provide a method for preparing a liposomal anthracycline glycoside composition, which is, at once, simple and straightforward.

Accordingly, the above objects and others which will become apparent in view of the following disclosure are provided by a method of preparing a liposomal anthracycline glycoside composition, which entails forming cardiolipin-containing liposomes by drying a lipid mixture containing cardiolipin, and then introducing an aqueous solution, and b) mixing the cardiolipin-containing liposomes with a solution of anthracycline glycoside.

DETAILED DESCRIPTION OF THE PREFERRED EMBODIMENTS

Figure 1:
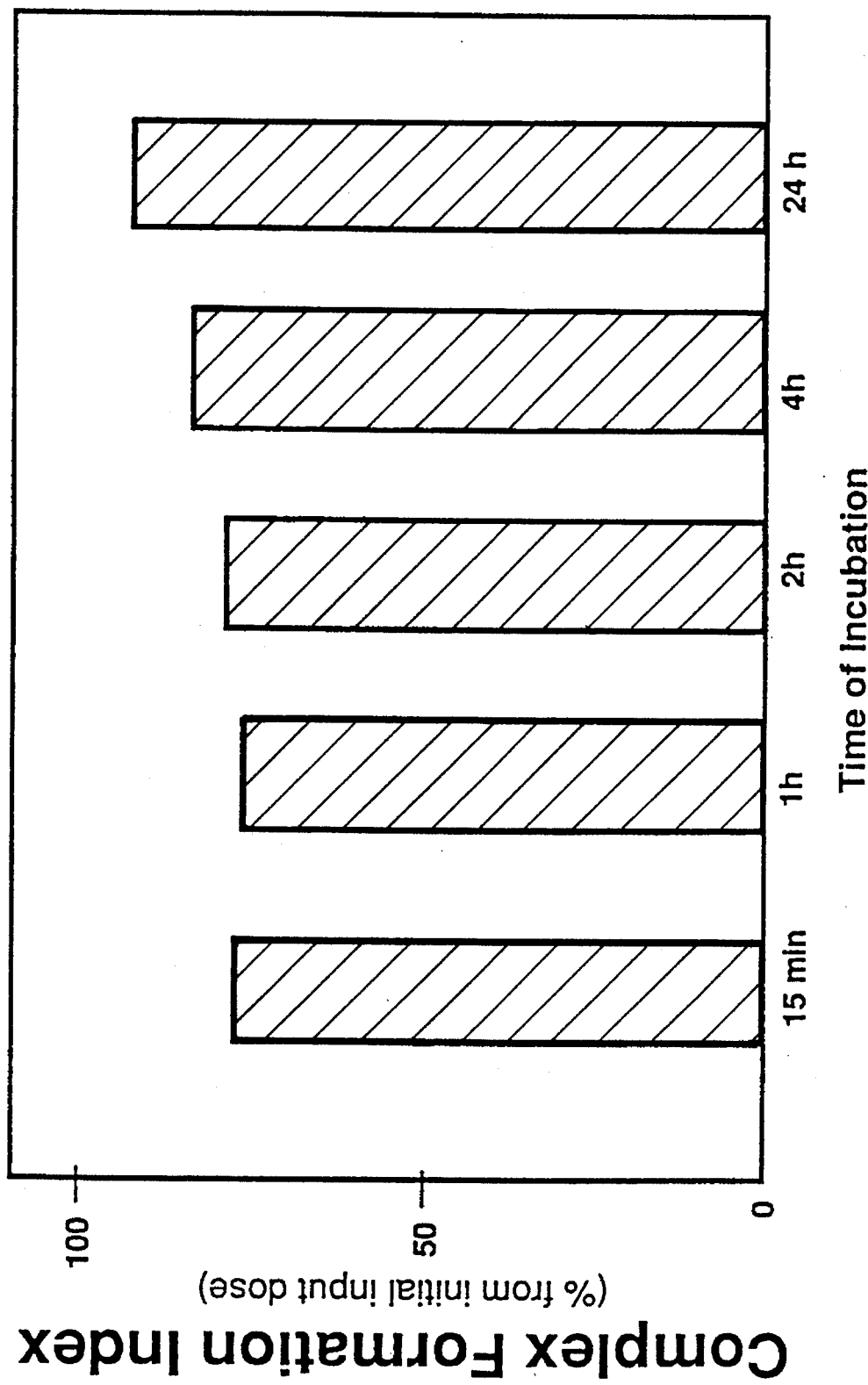
FIG. 1 illustrates evaluations of liposome-doxorubicin complex relative to the time of incubation at 25° C. following the mixing of both components.

In accordance with the present invention, it has been discovered that anthracycline glycosides may be encapsulated within liposomes in a surprisingly effective manner. The encapsulated anthracycline glycosides may then be injected into a mammalian host to effectively kill cancer cells with a reduced toxicity to the host body. In accordance with the present invention, any one or more anthracycline glycosides may be encapsulated. For example, actinomycin as described in U.S. Pat. No. 3,993,754, cis-platen analog as described by Perez-Solar R. Khokar Ar, Lopez-Berestein G. Treatment in Prophylaxis of Experimental Liver Metastases of M5076 Reticulosarcoma With Cis-Bisneodecanaoto-trans-R-1,2-diaminocyclohexane platinum (II) Encapsulated in Multi-lamellar Vesicles, Cancer Research. 1987, 47:6462-6 and doxorubicin as described in U.S. Pat. No. 4,419,398 may be so encapsulated to exhibit reduced inherent toxicities while preserving antitumor activity.

In accordance with the present invention, by the term "liposomes" is meant a closed structure composed of lipid bi-layers surrounding an internal aqueous space. It appears that the decreased cardiotoxicity when using liposomal-encapsulated doxorubicin, for example, is attributable to the fact that the liposomes do not accumulate in the heart in as great of a concentration as the free drug is believed to accumulate.

The present invention is, in part, directed to a liposomal anthracycline glycoside preparation which is based on a composition of one or more anthracycline glycosides and cardiolipin-containing liposomes. The present invention also pertains to a method of preparing such a composition.

Generally, the one or more anthracycline glycosides of the present invention may be any which exhibits antibiotic and/or oncolytic activity and which is characterized by cardiac tissue uptake in a mammalian host and by attendant cardiotoxicity and/or cardiomyopathy. Additionally, non-toxic and pharmaceutically acceptable analogs, derivatives or salts thereof may also be used. Further, as it is well-documented that doxorubicin hydrochloride (adriamycin) and daunorubicin are such anthracycline glycosides, they may also be used in the present invention. Thus, the present invention is explicitly limited to any specific embodiment of anthracycline glycoside.

Further, it is specifically within the ambit of the present invention to use analogs of anthracycline glycosides. Analogs of anthracycline glycosides which are used as anticancer agents are well known to those skilled in the art. In accordance with the present invention, any analog of an anthracycline glycoside may be used, which is presently used as an anticancer agent. For example, deoxy analogs, such as 7-deoxy-doxorubicin may be used. Epirubicin may also be used.

In accordance with the present invention, the cardiolipin-containing liposomes may be formed by drying a lipid mixture containing cardiolipin and then introducing an aqueous solution. Dispersion is completed by strongly homogenizing the mixture using a vortex, magnetic stirrer and/or sonication. The liposomes are negative liposomes considering the inherent negative charges of cardiolipin and that the lipid added to cardiolipin must be neutral or negative such as phosphatidyl choline, cholesterol, phosphatidyl serine or phosphatidyl glycerol. For better stability, however, the liposome preparation may be lyophilized.

In accordance with the present invention, the cardiolipin used may be obtained from either a natural or synthetic source as is known to those skilled in the art.

The present invention is, in part, predicated upon the discovery that anthracycline glycosides may be complexed to the cardiolipin-containing liposomes prior to clinical administration. Surprisingly, complexation is achieved by simply mixing cardiolipin-containing liposomes concentrate with a solution of anthracycline glycoside or by rehydration. For example, doxorubicin may be diluted in a 0.90% NaCl solution with 0.0017M phosphate buffer at pH of 7.4.

The anthracycline composition may be prepared also by two additional methods: 1) by rehydrating lyophilized cardiolipin-containing liposomes with a solution of anthracycline glycoside, or 2) by rehydrating with the buffer the mixture of lyophilized liposomes and crystalline doxorubicin.

The two additional methods described above may be practiced as follows. First, lyophilized cardiolipin-containing liposomes may be rehydrated with a solution of anthracycline glycoside. The cardiolipin-containing liposomes may be lyophilized using conventional methodologies. The rehydrating solution of anthracycline glycoside will have a concentration of at least about 15 µg/ml. Of course, all solutions described in the present specification are in pharmaceutically-acceptable solvents, such as saline solution of physiologically-acceptable concentration and pH and dextrose 5% saline.

Second, the present compositions may be prepared by rehydrating with buffer a mixture of lyophilized liposomes and crystalline doxorubicin. The buffer used may be those as generally described in the present specification.

Complexation of the anthracycline glycoside drug to cardiolipin-containing liposomes is due to the high binding affinity of such drugs, such as doxorubicin, to cardiolipin. From a pharmacological standpoint, the molar ratio of anthracycline glycoside to lipids may be adapted according to the type of tumor cells to be treated or the therapeutic end-point required. However, in order to obtain a good complexing efficiency, the cardiolipin content in liposomes should be at least half that of anthracycline glycoside added in terms of molar ratio. The complexed anthracycline glycoside-cardiolipin is strongly stabilized by an electrostatic interaction between two molecules of the glycoside and one molecule of cardiolipin and a stoichiometric interaction leading to a card pack dimer formation.

This strong binding allows for the insertion and the combination of the drug in the membrane lipids bilayer. Hence, the anthracycline glycoside is not situated at the surface of the liposome after complex formation but, rather, is firmly integrated in the liposome, which may then provide for a drug delivery that is as efficient as liposome-encapsulated anthracycline glycoside where the drug is contained in the internal aqueous phase or in the internal surface of the liposomes.

Surprisingly, liposome-complexed anthracycline glycosides prepared in accordance with the present invention present the same advantage as liposome-encapsulated doxorubicin from U.S. Pat. No. 4,419,348 in which the drug is first complexed and then encapsulated, regarding reduced cardiotoxicity. Thus, in accordance with the present invention, the procedure of preparing the liposomal-encapsulated doxorubicin as well as other anthracycline glycosides is greatly simplified, presenting advantages both in terms of scale-up and stability.

Having described the present invention, reference will now be made to certain examples which are provided solely for purposes of illustration and which are not intended to be limitative.

EXAMPLE 1

Preparation of a cardiolipin-containing liposome composition of the invention

Small unilamellar vesicles were formed by mixing 19.1 µmol cardiolipin, 96.2 µmol phosphatidyl choline and 64.6 µmol cholesterol. After thorough stirring, the mixture is evaporated to dryness in a 50 ml round-bottom flask using a rotary evaporator. The subsequent dried lipid film is resuspended in 10 ml sterile non-pyrogenic water. After a 30 min. swelling time, the resulting suspension was sonicated (Heat System, W220F) in a fixed temperature bath at 25° C. for 15 min. Liposomal preparation is then submitted to lyophilization with the trehalose, a sugar.

The following lipids were used: Phosphatidyl choline (egg), Cardiolipin (bovine), natural and/or synthetic and cholesterol. All of these materials are commercially available.

EXAMPLE 2

Preparation of an Anthracycline Cardiolipin Containing liposome composition with Doxorubicin Complex formation and integration of Doxorubicin into the lipid bilayer membrane of the cardiolipin-containing liposome was achieved prior to the clinical administration by simple vortex mixing of a vial containing 40 mg cardiolipin-liposome lyophilizate and 2.5 ml of a Doxorubicin solution previously prepared in 0.85% NaCl at 2 mg/ml. Vortex mixing is completed for 1 minute and mixture is kept at 37° C. for a 15 min. period incubation. Doxorubicin HCl was obtained from Adria Laboratories.

EXAMPLE 3

Determination of the Preferred Conditions of Incubation for Complexing Cardiolipin-Containing Liposomes to Doxorubicin Formation of the complex liposome-doxorubicin was evaluated relative to the time of the incubation at 25° C. following the mixing of both components (FIG. 1). Complexing index (expressed as percent of amount of doxorubicin complexed to liposomes from initial input dose) was determined following incubation after centrifugation of the mixture at 45,000 rpm for 30 min. at 4° C. and measurement of doxorubicin content in subsequent supernatant by spectrophotometry.

The results obtained show that a 15 min. incubation period was enough to obtain a satisfactory complex formation index of 77%. Longer exposure increase slightly the formation of the complex until 92% of the drug complexed after a 24 hr. incubation.

Association capacity of doxorubicin to cardiolipin-liposomes was evaluated for different concentrations of mixture of both components mixed in the same volume (5 ml) after an incubation of 15 min. at 37° C. at a fixed liposome/doxorubicin weight ratio of 11 (Table 1). The result obtained show that nearly all the drugs present in the incubation mixture was complexed to the cardiolipin-containing liposomes revealing an increase of complex formation when the incubation is carried out at 37° C. compared to an incubation temperature of 25° C. In addition, results demonstrate that even at a high dilution of both components (20 μg/ml of Dox and 0.22 mg/ml of liposomes) complex formation is very effective and nearly complete.

EXAMPLE 4

Study of the in vitro Drug Delivery Efficiency by Cardiolipin-Liposomes-Complexed Doxorubicin. Effect on Multidrug Resistance.

Resistance to major classes of cytotoxic drugs may emerge in tumor cells from patients treated by chemotherapy. Therefore, multidrug resistance may be one therapeutic obstacle in cancer treatment. It has been shown that liposome-encapsulated doxorubicin may modulate multidrug resistance in cancer cells. (A. R. Thierry, T. J. Jorgensen, D. Forst, I. A. Belli, A. Dritschilo, A. Rahman. *Modulation of Multidrug Resistance in Chinese Hamster Cells by Liposome-encapsulated Doxorubicin.* Cancer Comm. Vol. 1 pp. 311–316. (1989)). The capability to increase Doxorubicin activity in multidrug resistant cells was due to the use of a liposomal carrier. This capability was studied when cardiolipin-liposome-complexed doxorubicin. Thus, multidrug resistance reversal ability bore witness to the integrity or stability of the cardiolipin-liposome-doxorubicin complex.

Clonogenic assay was performed to evaluate modulation of multidrug resistance of free doxorubicin, cardiolipin-liposome-complexed doxorubicin and liposome-encapsulated doxorubicin in MCF-7/ADR and LZ cells which are resistant to doxorubicin. MCF-7/ADR and LZ cells are multidrug resistant cell lines originating from human breast cancer and Chinese hamster fibroblast,respectively.

An accurately known number of cells plated in a 10cm$^2$ culture cell were treated for 4 hrs. at different drug concentrations. Following exposure, cells were washed twice with PBS and fresh culture medium was added. The cells were left for a 15 day incubation period to develop colonies. The resulting colonies were then stained with methylene blue and counted. Percent survival of treated cells was determined relative to untreated control. Cytotoxic activity was expressed as IC$_{50}$ which was defined as the concentration of drug resulting in 50% survival of the colonies compared to control.

Figure 2:
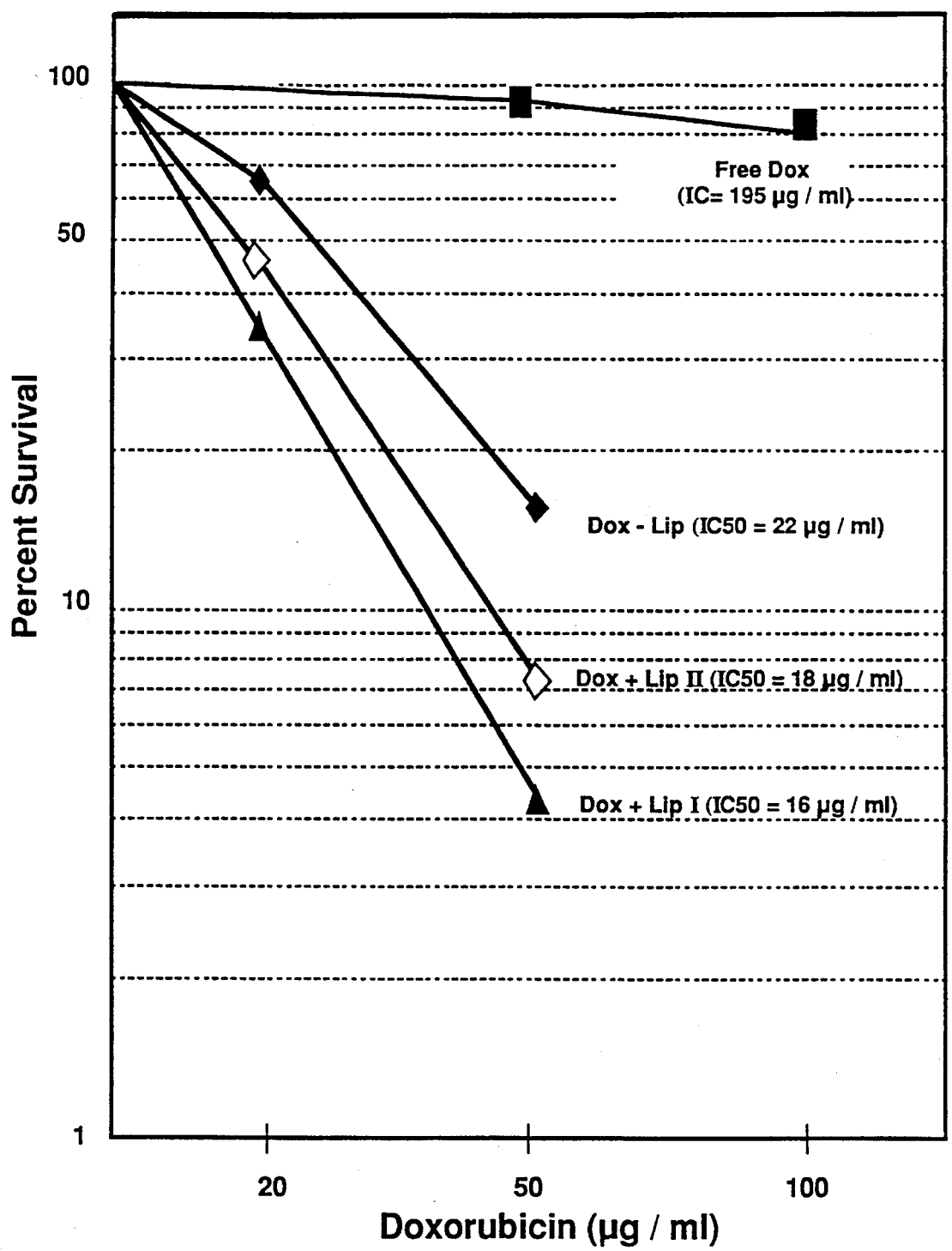
FIG. 2 illustrates a comparison of cytotoxicity of free doxorubicin, liposome-encapsulated doxorubicin and cardiolipin-liposome-complex doxorubicin using LZ cells.

In FIG. 2, cytotoxicity of free doxorubicin, liposome-encapsulated doxorubicin, and the cardiolipin-liposome-complexed doxorubicin were compared using LZ cells. In Dox+Lip I treatment, cells were exposed to cardiolipin-liposome-complexed doxorubicin which was prepared from mixing drug to a concentrate of previously formed cardiolipin-liposomes. Dox+Lip II correspond to cardiolipin-liposome-complexed doxorubicin which was prepared from mixing drug to a cardiolipin-liposome lyophilizate. The three liposomal doxorubicin preparations used in this experiment exhibited comparable cytotoxicity against LZ cells and thus a comparable drug resistance reversal capacity (approximately 9-fold compared to free drug in terms of IC$_{50}$).

Figure 3:
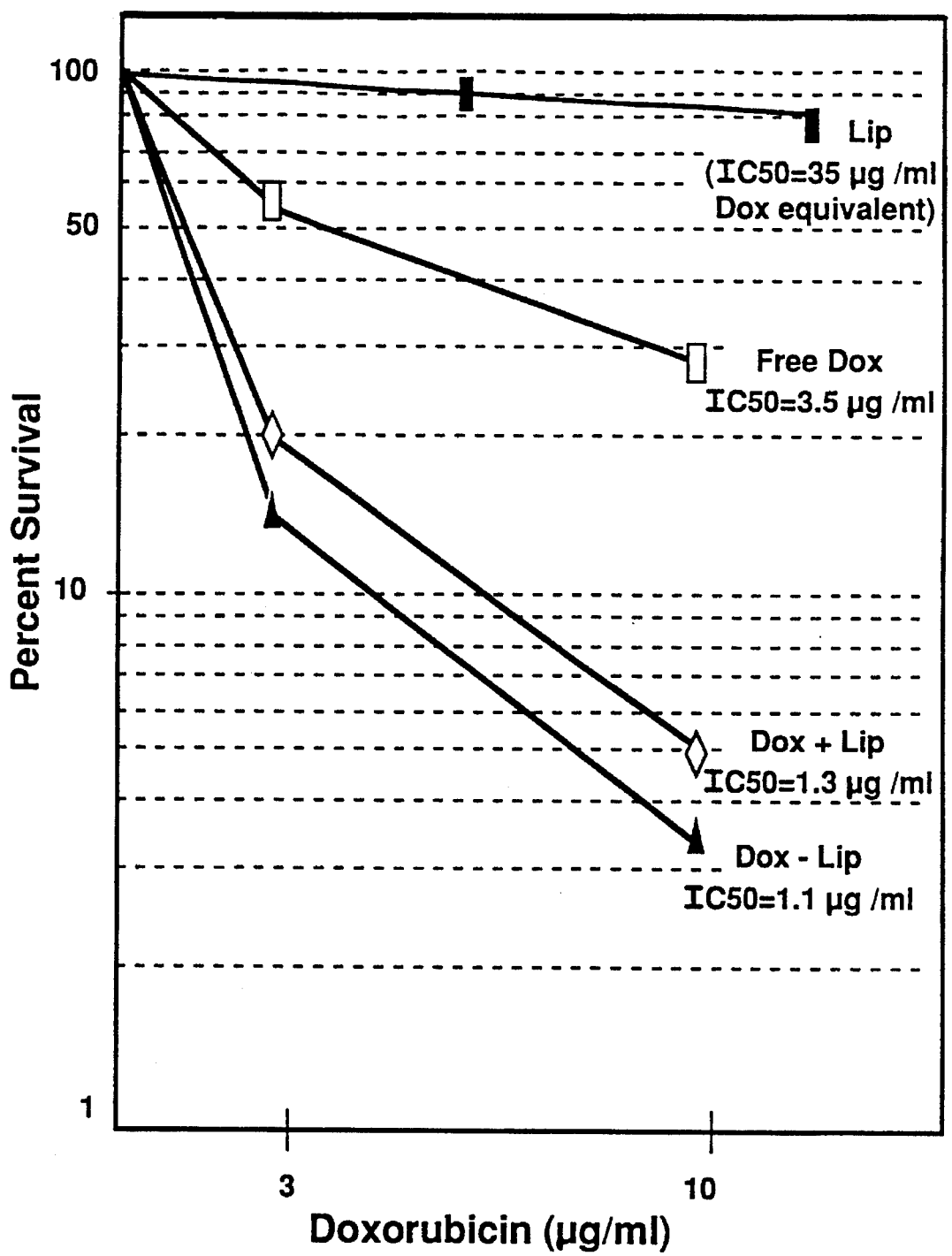
FIG. 3 illustrates survival curves of MCF-7/ADR cells treated with free doxorubicin, empty liposomes, cardiolipin-liposomes and doxorubicin in simultaneous combinations with empty cardiolipin-liposomes.

Survival curves of MCF-7/ADR cells treated with free Doxorubicin, empty liposomes, cardiolipin-liposomes and doxorubicin in simultaneous combinations with empty cardiolipin-liposomes are shown in FIG. 3. In this experiment cardiolipin-liposomes were complexed with free doxorubicin directly in the culture medium (volume 5 ml) before cell treatment and cardiolipin-liposomes concentration added to the drug was equal to that present at equivalent doxorubicin concentration in liposome-encapsulated doxorubicin. Both liposomal doxorubicin preparations present a comparable cytotoxic effect and thus a comparable drug resistance reversal effect. It was established in the human breast carcinoma resistant MCF-7/ADR cell line that both liposomal doxorubicin preparations have the same cytotoxic activity revealing that the drug in the cardiolipin-liposome-complex is as well integrated as in the liposome-encapsulated drug.

Figure 4:
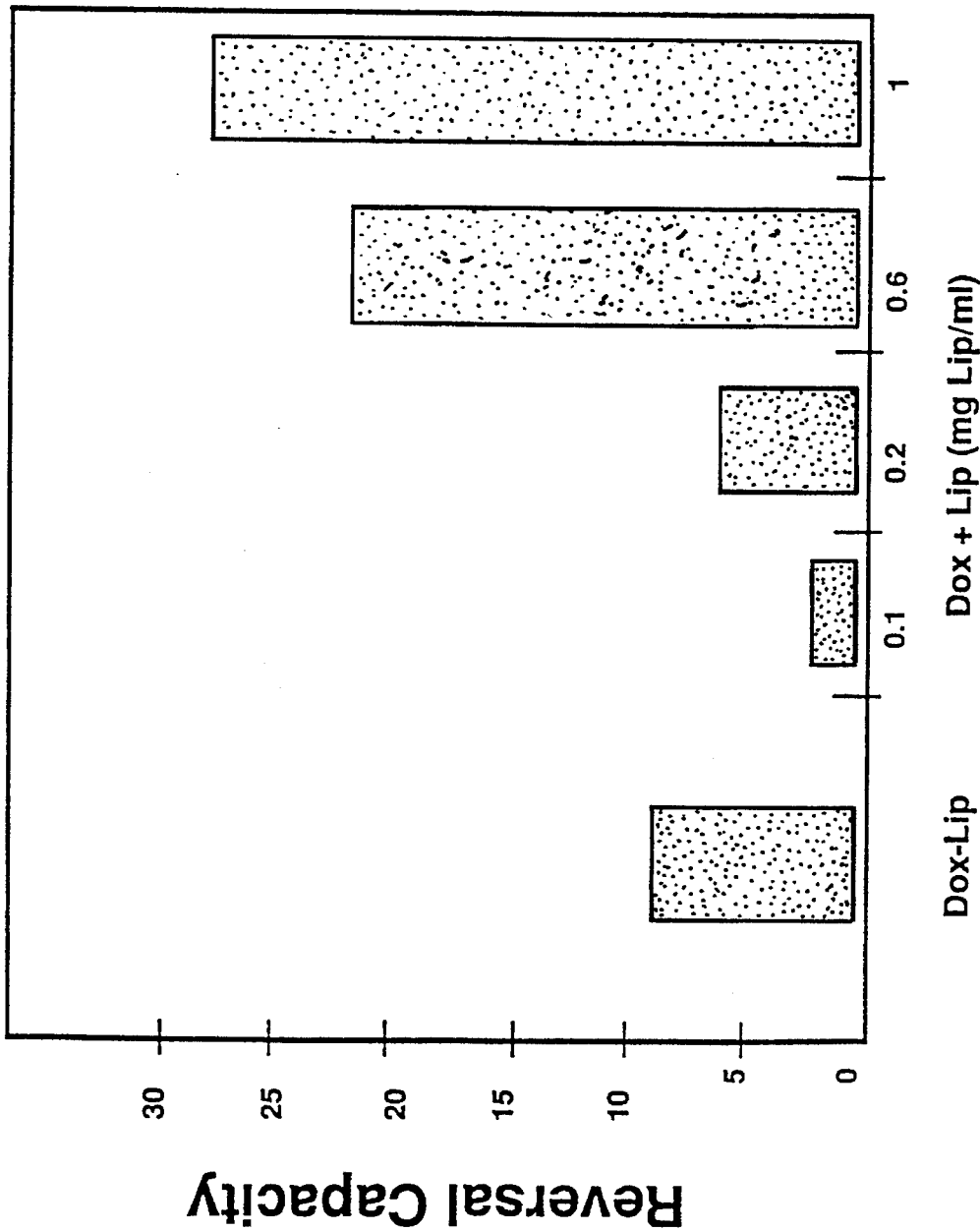
FIG. 4 illustrates the reversal capacity of multidrug resistance by various treatments in LZ cells with liposome-encapsulated doxorubicin in LZ cells.

FIG. 4 shows the reversal capacity of various treatments in the LZ cells. Generally, reversal capacity to multidrug resistance refers to the level at which drug resistance is overcome and is measured by the ratio of these amounts for free drug/liposome-encapsulated drug. For example, if 5 mg of free drug or 1 mg of liposome-encapsulated drug are required to overcome resistance to a drug, a reversal capacity of 5 is indicated. This would generally indicate that the liposome-encapsulated drug is five times as effective as the free drug in a drug-resistant host. Results demonstrate that increased concentrations of liposome in combination with Doxorubicin, for example substantially enhance the cytotoxic effect of the drug. As shown previously, liposome encapsulated doxorubicin seems to be approximately as cytotoxic as cardiolipin-liposome-complexed doxorubicin when liposome concentration (0.2 mg/ml) added to drug was equal to that present at equivalent drug concentration. For example, when 0.6 mg/ml and 1.0 mg/ml of liposomes (concentration corresponding to 90% and 50% survival for liposome cytotoxicity alone in LZ cells) are added to doxorubicin the reversal capacity of these treatments are 22 and 28 fold, respectively, showing a higher reversal capacity compared to liposome encapsulated doxorubicin (9-fold).

Evidence of the role of the complexed cardiolipin-liposome-doxorubicin on multidrug resistance is demonstrated in FIG. 2. LZ cells were exposed to different concentrations of cardiolipin-liposome-complexed doxorubicin corresponding to a liposome/doxorubicin weight ratio of 11. As previously observed, drug is nearly all complexed to the liposome when incubated at 37° C. and the liposomal doxorubicin preparation exerts a cytotoxic effect higher than that of free drug. When vincristine (an alkaloid anticancer agent) is mixed in the same conditions as Doxorubicin to cardiolipin-containing liposomes, no association between drug and liposome was formed and no increase in drug cytotoxicity was observed. The results demonstrate that cardiolipin-liposome complexed specifically doxorubicin and that this association is responsible for the increase of cytotoxicity against multidrug resistant cells.

In addition to the surprising advantages described above, the present invention also affords all of the advantages previously obtainable with liposomal anthracycline glycoside compositions. Notably, reference may be made to U.S. Pat. No. 4,419,348, which is incorporated herein in the entirety. Further, the following experiments illustrate the adaptability and versatility of the present method of making blank cardiolipin containing liposomes and their effective and efficient internalization of the drug inside the liposomes because of the strong affinity of the specific lipid to doxorubicin. The present method of preparing liposomes not only greatly simplifies the industrial manufacturing but actual patient treatment because of the usefulness of the method near the bed side of a patient as has been demonstrated by the spontaneous internalization of doxorubicin to the lyophilized and reconstituted liposomes.

Finally, in accordance with the present invention, it is noted that high yields of encapsulation may be obtained even if very dilute solutions of liposome and anthracycline glycoside or analog thereof are used. For example, solutions of liposome which are as dilute as 0.5 mg/ml, preferably at least 0.10 mg/ml may be used.

With respect to the solution of anthracycline glycoside or analog thereof, solutions as dilute as 5 µg/ml, preferably 10 µg/ml, may be used.

More preferably, however, a solution concentration of liposomes of at least 0.20 mg/ml is used, and a solution concentration of anthracycline glycoside or analog thereof of at least 15 µg/ml is used.

Of course, higher solution concentrations of each may be used as desired.

Additionally, it is specifically contemplated in the present invention that the same may be practiced with a single anthracycline glycoside or analog thereof or a mixture of two or more anthracycline glycosides or analogs thereof.

Further, in accordance with the present invention, pharmaceutical compositions are provided which contain, at least, one or more liposomal anthracycline glycoside compositions and a pharmaceutically acceptable carrier. It is, further, explicitly contemplated that these pharmaceutical compositions may contain a mixture of different liposomal anthracycline glycosides.

Finally, as indicated above, in accordance with the present invention, it is now possible to obtain an effective treatment against different types of cancer cells by modulating the ratio of anthracycline glycoside/liposome as a function of the type of cancer cells to be treated.

TABLE 1

Combined treatment of Lip with Dox or VCR Cytotoxic Effect in LZ Cells and Binding Capacity of Lip or Dox or VCR

| DRUG CONCENTRATION µg/ml | LIP CONCENTRATION in drug cyto- toxicity mg/ml | DOX + LIP | | VCR + LIP | |
|---|---|---|---|---|---|
| | | % free drug in the medium after incubation | fold increase in drug cytotoxicity | % free drug in the medium | Fold increase in drug cytotoxicity |
| 20 | 0.22 | 1.5 | 1.6 | 99.3 | 1.1 |
| 50 | 0.55 | 4.4 | 5.9 | 98.5 | 1.0 |
| 100 | 1.10 | 3.5 | 8.4 | 98.1 | 1.1 |
| 150 | 1.65 | 2.9 | 34.4 | 97.9 | 1.7 |

The fold increase noted in Table 1 was determined as the ratio of $IC_{50}$ of the drug to that of the combined treatment of the drug and Lip % free drug in the medium after incubation was determined as described above.

Additionally, a most important aspect of the present invention resides in the discovery that very high yields of anthracycline glycoside complexation may be obtained. Generally, complexation (encapsulation) yields of at least 75% anthracycline glycoside may be obtained. However, preferably a yield of at least 95% is obtained.

Generally, the yield of complexation is increased by prolonging the time with which the various constituent ingredients are mixed in the complexation mixture.

Furthermore, although the preferred ratio of cardiolipin used to anthracycline glycoside will vary from glycoside to another, in general a molar ratio of glycoside to cardiolipin of about 3:1 to 1.5:1 is used, preferably, however, about 2:1.

In general, for any particular type of cancer, malignant cells thereof may be cultured in vitro and subjected to various ratios of anthracycline glycoside/liposome in order to determine the most effective ratio. This ratio affording the best results may then be used with the in vivo method of treatment for the patient. In using this selection method, conventional culturing techniques may be used for cultivating the malignant cells in vitro. Further, this method may be applied to virtually any form of cancer. The many forms of cancer are well known to those skilled in the art.

For example, the present invention may be used to prepare liposomal anthracycline glycoside compositions which may be used in the treatment of carcinomas, sarcomas or leukemia and lymphoma. Generally, carcinoma refers to any cancer of epithelial tissues including body surfaces, digestive tracts and organs originating therefrom. Sarcoma refers generally to any cancer of non-epithelial supportive tissues. Leukemia and lymphoma are non-epithelial malignant tumors which can be included within the group of sarcomas in a broad sense. However, they are cancers of wandering cells appearing in the blood and are considered apart from fixed sarcomas.

Further, as examples of solid tumors, i.e. carcinomas or sarcomas, may be mentioned tumors of the gullet, oral cavity, stomach, duodenum, small intestine, large intestine, anus, gall bladder, labium, nasopharynx, liver, skin, pancreas, bronchus, lung, mammary gland, uterus, ovary, prostate gland, male reproductive organ and urinary organs, such as the bladder and kidney.

Furthermore, the liposomal anthracycline glycosides of the present invention may include within pharmaceutical compositions which include other ingredients, such as known stabilizers, buffers, surfactants, excipients as well as other active ingredients which are used in the treatment of cancer. Such additional ingredients are well known to those skilled in the art.

The compositions of the present invention may be administered in any manner, such as, for example, intravenously, a intraperitoneally or orally, if desired.

Having described the present invention, it will be apparent that many changes and modifications may be made to the above-described embodiments without departing from the spirit and the scope of the present invention.

What is claimed as new and desired to be secured by Letters Patent of the United States is:

1. A method for encapsulating in a cardiolipin-containing liposome an anthracycline glycoside, selected from the group consisting of doxorubicin and daunorubicin, consisting of the step of
    a) mixing said cardiolipin-containing liposomes with an aqueous-based liquid comprising said anthracycline glycoside for a time sufficient to effect encapsulation of said anthracycline glycoside in said cardiolipin-containing liposome,
    whereby said anthracycline glycoside is encapsulated in said cardiolipin-containing liposome.

2. The method of claim 1, wherein said liposome comprises at least one neutrally or negatively charged lipid.

3. The method of claim 2, wherein said at least one lipid is phosphatidyl choline, cholesterol, phosphatidyl serine or phosphatidyl glycerol.

4. The method of claim 1, wherein said mixing is by vortex magnetic stirring, sonication or combination thereof.

5. The method of claim 1, wherein at least about 75% the anthracycline glycoside complexes with the cardiolipin-containing liposomes.

6. The method of claim 1, wherein at least about 75% of said anthracycline glycoside is encapsulated within said cardiolipin-containing liposome.

7. The method of claim 6, wherein at least about 95% of said anthracycline glycoside is encapsulated within said cardiolipin-containing liposome.

8. The method of claim 7, wherein said mixing is effected for at least about 24 hours.

9. The method of claim 1, wherein a molar ratio of anthracycline glycoside to cardiolipin is about 3:1 to about 1.5:1.

10. The method of claim 9, wherein a molar ratio of said anthracycline glycoside to cardiolipin is about 2:1.

11. The method of claim 1, wherein said mixture has a concentration of liposomes of at least about 1.0 mg/ml.

12. The method of claim 11, wherein said mixture has a concentration of liposomes of at least about 2.0 mg/ml.

13. The method of claim 1, wherein said aqueous-based anthracycline glycoside liquid has a concentration of anthracycline glycoside of at least about 5 µg/ml.

14. The method of claim 13, wherein said aqueous-based anthracycline glycoside liquid has a concentration of anthracycline glycoside of at least about 10 µg/ml.

15. The method of claim 1, wherein said aqueous-based liquid comprises a saline solution, of physiologically-acceptable concentration and pH, and dextrose 5%.

16. A method for encapsulating in a cardiolipin-containing liposome an anthracycline glycoside selected from the group consisting of doxorubicin and daunorubicin, consisting of the step of
    a) rehydrating a mixture of (i) lyophilized cardiolipin-containing liposomes and (ii) said anthracycline glycoside in crystalline form by mixing therewith an aqueous-based liquid in amount sufficient to effect said rehydration,
    whereby said anthracycline glycoside is encapsulated in said cardiolipin-containing liposome.

17. The method of claim 16, wherein at least about 75% of said anthracycline glycoside is encapsulated within said cardiolipin-containing liposome.

18. The method of claim 17, wherein at least about 95% of said anthracycline glycoside is encapsulated within said cardiolipin-containing liposome.

19. The method of claim 16, wherein said mixing is effected for at least about 15 minutes.

20. The method of claim 19, wherein said mixing is effected for at least about 24 hours.

21. The method of claim 16, wherein said aqueous-based liquid comprises a saline solution, of physiologically-acceptable concentration and pH, and dextrose 5%.

22. The method of claim 16, wherein a molar ratio of said anthracycline glycoside to cardiolipin is about 1:3 to about 1.5:1.

23. The method of claim 22, wherein a molar ratio of said anthracycline glycoside to cardiolipin is about 2:1.

24. The method of claim 1, where said cardiolipin-containing liposome is lyophilized and said mixing effects rehydration of said lyophilized, cardiolipin-containing liposomes.

25. A method for encapsulating in a cardiolipin-containing liposome an anthracycline glycoside, selected from the group consisting of doxorubicin and daunorubicin, comprising the steps of
    a) providing said cardiolipin-containing liposomes and said anthracycline glycoside; and
    b) mixing said cardiolipin-containing liposomes with an aqueous-based liquid comprising said anthracycline glycoside for a time sufficient to effect encapsulation of said anthracycline glycoside in said cardiolipin-containing liposome,
    whereby said anthracycline glycoside is encapsulated in said cardiolipin-containing liposome.

26. The method of claim 25, wherein at least about 75% of said anthracycline glycoside is encapsulated within said cardiolipin-containing liposomes.

27. The method of claim 25, wherein at least about 95% of said anthracycline glycoside is encapsulated within said cardiolipin-containing liposomes.

* * * * *